United States Patent
Rom

(10) Patent No.: US 7,963,924 B2
(45) Date of Patent: Jun. 21, 2011

(54) HEART SIMULATOR

(75) Inventor: Rami Rom, Zichron Yaacov (IL)

(73) Assignee: Sorin CRM SAS, Clamart (FR)

( * ) Notice: Subject to any disclaimer, the term of this patent is extended or adjusted under 35 U.S.C. 154(b) by 825 days.

(21) Appl. No.: 11/552,583

(22) Filed: Oct. 25, 2006

(65) Prior Publication Data
US 2008/0103744 A1     May 1, 2008

(51) Int. Cl.
*A61B 5/02* (2006.01)
(52) U.S. Cl. .................. 600/508; 607/9; 703/11
(58) Field of Classification Search .......... 607/17, 607/18, 25, 30, 31, 59; 600/510, 508; 703/11
See application file for complete search history.

(56) References Cited

U.S. PATENT DOCUMENTS

| | | | |
|---|---|---|---|
| 3,833,865 A | | 9/1974 | Palmer |
| 4,825,869 A | * | 5/1989 | Sasmor et al. ............... 607/27 |
| 5,692,907 A | * | 12/1997 | Glassel et al. .............. 434/262 |
| 6,459,929 B1 | | 10/2002 | Hopper et al. |
| 7,558,627 B1 | * | 7/2009 | Turcott ....................... 607/27 |
| 2006/0224204 A1 | * | 10/2006 | Hettrick et al. .............. 607/23 |

FOREIGN PATENT DOCUMENTS

| | | |
|---|---|---|
| WO | 2005007075 A2 | 1/2005 |
| WO | 2006061822 A2 | 6/2006 |

OTHER PUBLICATIONS

Whinnett et al, "Haemodynamic effects of changes in AV and VV delay in cardiac resynchronization therapy", Heart, published online May 18, 2006, doi:10.1136/hrt.2005.080721.

* cited by examiner

*Primary Examiner* — Niketa I Patel
*Assistant Examiner* — Hiba El-Kaissi
(74) *Attorney, Agent, or Firm* — Simon Kahn

(57) ABSTRACT

A development system for a cardiac pacemaker control system, the development system comprising: a cardiac pacemaker prototype including an adaptive control system; and a heart simulator in communication with the cardiac pacemaker prototype comprising: a means for receiving pacing stimulations output from the cardiac pacemaker prototype; and a hemodynamic sensor model responsive to the received pacing stimulations, the hemodynamic sensor model being operable to output a signal simulating a hemodynamic sensor in a plurality of heart states, the hemodynamic sensor model being further operative to output the signal simulating the hemodynamic sensor in the plurality of heart states in a plurality of heart conditions.

20 Claims, 9 Drawing Sheets

HEART SIMULATOR

BACKGROUND OF THE INVENTION

The invention relates generally to the field of heart simulators, and in particular to a simulator providing temporally dependent waveforms simulating implanted hemodynamic sensor signals.

Cardiac resynchronization therapy (CRT) is an established therapy for patients with congestive systolic heart failure and intraventricular electrical or mechanical conduction delays. CRT is based on synchronized pacing of the two ventricles according to the sensed natural atrium signal that determines the heart rhythm. The resynchronization task demands exact timing of the heart chambers so that the overall stroke volume is maximized for any given heart rate (HR). Optimal timing of activation of the two ventricles is one of the key factors in determining cardiac output. The two major timing parameters which are programmable in a CRT device and determine the pacing intervals are the atrioventricular (AV) delay and interventricular (VV) interval. The AV delay is defined herein as the delay from an atrial event that triggers filling of the atrium to a ventricular event that triggers blood ejection from the ventricle. The VV interval is defined herein as the interval between the pacing signal for the left ventricle to the pacing signal for the right ventricle.

Rate responsive pacemakers were designed in the 1980's and 1990's that allow the atrial pacing rate to automatically change according to combined inputs from two implanted sensors typically, accelerometer and minute ventilation sensors. The rate responsive system give a more physiologic pacing to Bradycardia patients and allow higher cardiac output at exercise conditions.

Zachary I. Whinnett et al in "Haemodynamic effects of changes in AV and VV delay in cardiac Resynchronization Therapy show a consistent pattern: analysis of shape, magnitude and relative importance of AV and VV delay", Heart published online, 18 May 2006, doi:10.1136/hrt.2005.080721, studied the importance of the AV delay and VV interval optimization in CHF patients. The authors conclude that changing the AV and VV delay result in a curvilinear and reproducible acute blood pressure response. This shape fits very closely to a parabola which may be helpful in designing a streamlined clinical protocol to select optimal AV and VV delay.

Various types of implantable electrodes are currently available which generate intra-cardiac electrograms (IEGMs). These electrodes are bi-directional and are capable of both outputting electrical signals reflecting heart electrical activity and receiving electrical impulses to affect heart activity. Various types of hemodynamic sensors are also available reflecting heart mechanical behavior, including without limitation, impedance sensors, pressure sensors and cardiac wall accelerometers, QT interval sensors and non-invasive hemodynamic sensors. However, there are currently no commercially available CRT devices that modify the AV delay and VV interval responsive to the implanted hemodynamic sensors in an adaptive, closed loop system. The ability to design and validate such system is a major technological hurdle for developing and bringing to market closed loop physiological pacemakers and defibrillators that will deliver optimal therapy to CHF and other heart disease patients. In particular the design and validation of the control system which processes the data and makes the appropriate adaptation and classification of patient condition on-line would be greatly enhanced by an appropriate simulator.

Cardiac Output (CO) is defined as the blood volume in milliliters pumped by the heart in one minute. HR and stroke volume, defined as milliliters of blood pumped/systole, determine CO. CO is influenced by the autonomic nervous system in that 1) sympathetic stimulation increases heart rate and stroke volume and 2) parasympathetic stimulation slows heart rate. CO is also influenced by increased venous return, as would occur during exercise. The increased venous return causes greater stretch of the cardiac fibers resulting in greater contraction (i.e., increased stroke volume). This increase in stroke volume due to increased venous return is called Frank-Starling law of the heart.

Contractility of the heart is a major determinant of its ability to pump blood around the body, which is required for the functions of all organs. Because the heart is a muscle, it can adapt to different conditions/requirements that directly affect its contractility and efficiency.

U.S. Pat. No. 3,833,865 to Palmer, issued Sep. 3, 1974, the entire contents of which is incorporated herein by reference, is addressed to a heart simulator which generates an electric waveform similar to that produced by the human heart. Unfortunately such a device is neither responsive to the output of an adaptive CRT device, nor is their any provision for hemodynamic sensor simulation.

U.S. Provisional patent application Ser. No. 60/656,392 filed Feb. 28, 2005 to Rom, entitled "Adaptive Cardiac Resynchronization Therapy and Vagal Stimulation System", the entire contents of which is incorporated herein by reference, is addressed to a method an apparatus for optimizing cardiac resynchronization therapy devices and vagal stimulators.

U.S. Provisional patent application Ser. No. 60/685,464 filed May 27, 2005 to Rom, entitled "Ventricle Pacing During Atrial Fibrillation Episodes", the entire contents of which is incorporated herein by reference, is addressed to a system that learns to associate ventricle-atrial intervals with temporal patterns of at least one hemodynamic sensor using neural network processing.

U.S. Provisional patent application Ser. No. 60/897,513 to Rom, entitled "Intelligent Control System for Adaptive Cardiac Resynchronization Therapy Devices" filed Jul. 17, 2006 to Rom, the entire contents of which is incorporated herein by reference, is addressed to an adaptive CRT control system that achieves optimal AV delay and VV pacing intervals with temporal patterns of stroke volume comprising a learning module and an algorithmic controller module supervising the learning module.

International patent application S/N PCT/IL2004/000659 published Jan. 25, 2005 as WO 2005/007075 to Rom, entitled "Adaptive Resynchronization Therapy System", and filed as U.S. patent application Ser. No. 10/565,279 Jan. 20, 2006, the entire contents of each of which is incorporated herein by reference, is addressed to a system including a learning module and an algorithmic module for learning a physiological aspect of a patient body and regulating the delivery of a physiological agent to the body. Such an adaptive system is advantageous however its development and validation would be simplified by the existence of a heart simulator providing signals simulating hemodynamic sensors.

Thus there is a need for a heart simulator that generates simulated IEGMs and simulated hemodynamic sensor outputs. Preferably the simulated outputs would be responsive to an adaptive CRT device. Such a heart simulator would be particularly useful for the development of closed loop pacemaker and defibrillator controllers working according to implanted hemodynamic sensors thereby shortening the lead time before in-vivo pre-clinical and clinical experiments can begin.

SUMMARY OF THE INVENTION

Accordingly, it is a principal object of the present invention to overcome the disadvantages of prior art heart simulators. This is provided for in the present invention by a heart simulator that generates simulated implanted IEGM signals and hemodynamic sensor signals thereby simulating both heart electrical and mechanical activity, the simulation signals being responsive to the output of a CRT device. Preferably, the heart simulator further exhibits a programming input, allowing for simulation of various heart action irregularities.

The invention provides for a development system for a cardiac pacemaker control system, the development system comprising: a cardiac pacemaker prototype including an adaptive control system; and a heart simulator in communication with the cardiac pacemaker prototype comprising: a means for receiving pacing stimulations output from the cardiac pacemaker prototype; and a hemodynamic sensor model responsive to the received pacing stimulations, the hemodynamic sensor model being operable to output a signal simulating a hemodynamic sensor in a plurality of heart states, the hemodynamic sensor model being further operative to output the signal simulating the hemodynamic sensor in the plurality of heart states in a plurality of heart conditions.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1:
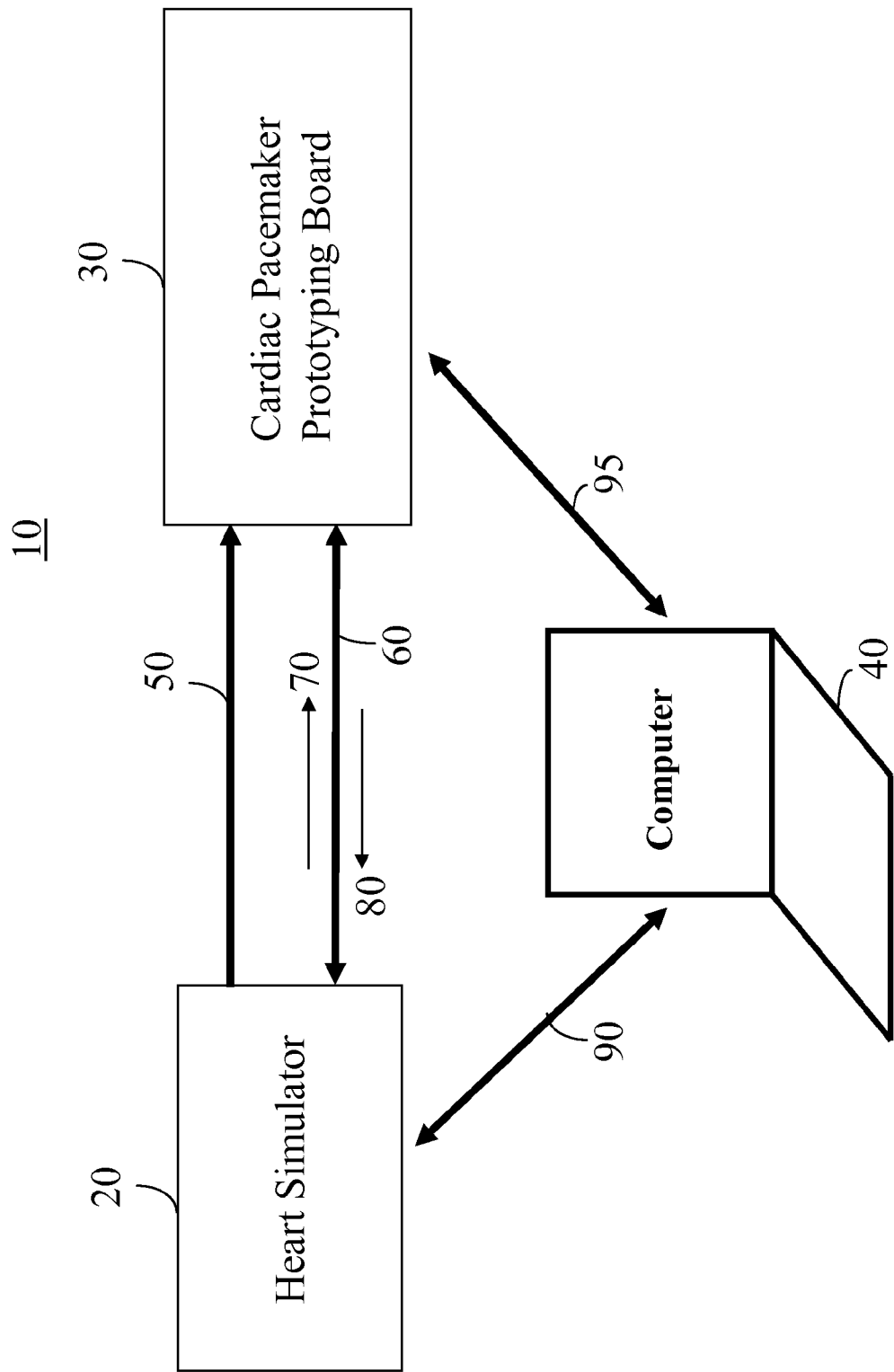
FIG. 1 illustrates a high level block diagram of a system for design verification of a cardiac pacemaker comprising a heart simulator in accordance with a principle of the current invention.

The present embodiments enable a heart simulator that generates simulated implanted IEGM signals and hemodynamic sensor signals thereby simulating both heart electrical and mechanical activity, the simulation signals being responsive to the output of a CRT device. Preferably, the heart simulator further exhibits a programming input, allowing for simulation of various heart action irregularities.

The aim of the heart simulator is to allow the design and testing of a prototype pacemaker and hence it is advantageous that the heart simulator be responsive to outputs of the prototype pacemaker and be versatile enough to simulate various physiological phenomenon that may occur in a real heart and be close enough to the appropriate physiological signal to aid in pacemaker development. The sensor model does not have to mimic exact patient behavior and exact specific values, particularly if used in the development of a pacemaker comprising a neural network which learns from the response of the attached heart.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 illustrates a high level block diagram of a system 10 for design verification of a cardiac pacemaker comprising a heart simulator 20, a cardiac pacemaker prototyping board 30 and a computing device 40 in accordance with a principle of the current invention. Heart simulator 20 outputs a simulated hemodynamic sensor signal 50 for input to cardiac pacemaker prototyping board 30 and further exhibits a bidirectional IEGM path 60 which carries both a simulated IEGM 70 from heart simulator 20 to cardiac pacemaker prototyping board 30, preferably comprising an cardiac pacemaker in development having an adaptive control system, and a pacing stimulation 80 generated by cardiac pacemaker prototyping board 30 to heart simulator 20. In an exemplary embodiment simulated IEGM 70 output by heart simulator 20 and simulated hemodynamic sensor signal 50 are responsive to pacing stimulation 80 received by heart simulator 20 from cardiac pacemaker prototyping board 30. Computing device 40 is connected by a bidirectional data path 90 to heart simulator 20 and by a bidirectional data path 95 to cardiac pacemaker prototyping board 30. Simulated IEGM 70, pacing stimulation 80 and simulated hemodynamic sensor signal 50 may each represent a plurality of signals without exceeding the scope of the invention.

In operation, cardiac pacemaker prototyping board 30 receives simulated IEGM 70 and simulated hemodynamic sensor signal 50 from heart simulator 20. In an exemplary embodiment in which cardiac pacemaker prototyping board 30 comprises a learning module as described in international patent application S/N PCT/IL2004/000659 published Jan. 25, 2005 as WO 2005/007075 to Rom, entitled "Adaptive Resynchronization Therapy System" referenced above, cardiac pacemaker prototyping board 30 is operative to learn the heart condition as indicated by the received simulated IEGM 70 and simulated hemodynamic sensor signal 50 and in response deliver appropriate pacing stimulation 80 to heart simulator 20 through bidirectional IEGM path 60.

Heart simulator 20 is programmable to a predetermined condition by computing device 40 via bidirectional data path 90, and in response outputs signals representative of the predetermined electrical heart condition via simulated IEGM 70 and the predetermined mechanical heart condition via simulated hemodynamic sensor signal 50. Heart simulator 20 is further responsive to pacing stimulation output by cardiac pacemaker board 30 via pacing stimulation 80 to change the simulated heart condition as indicated by simulated IEGM 70 and simulated hemodynamic sensor signal 50.

Computing device 40 enables the presentation in real time of data from both heart simulator 20 and cardiac pacemaker prototyping board 30 and can also run test codes on heart simulator 20 and test the design performance of cardiac pacemaker prototyping board 30. In one embodiment, cardiac pacemaker prototyping board 30 is provided with a wireless communication device for wireless data transfer to computing device 40, and thus bidirectional data path 95 represents a wireless path. Data accumulated in cardiac pacemaker prototyping board 30 is transferred to computing device 40 for performance monitoring via bidirectional data path 95.

Figure 2:
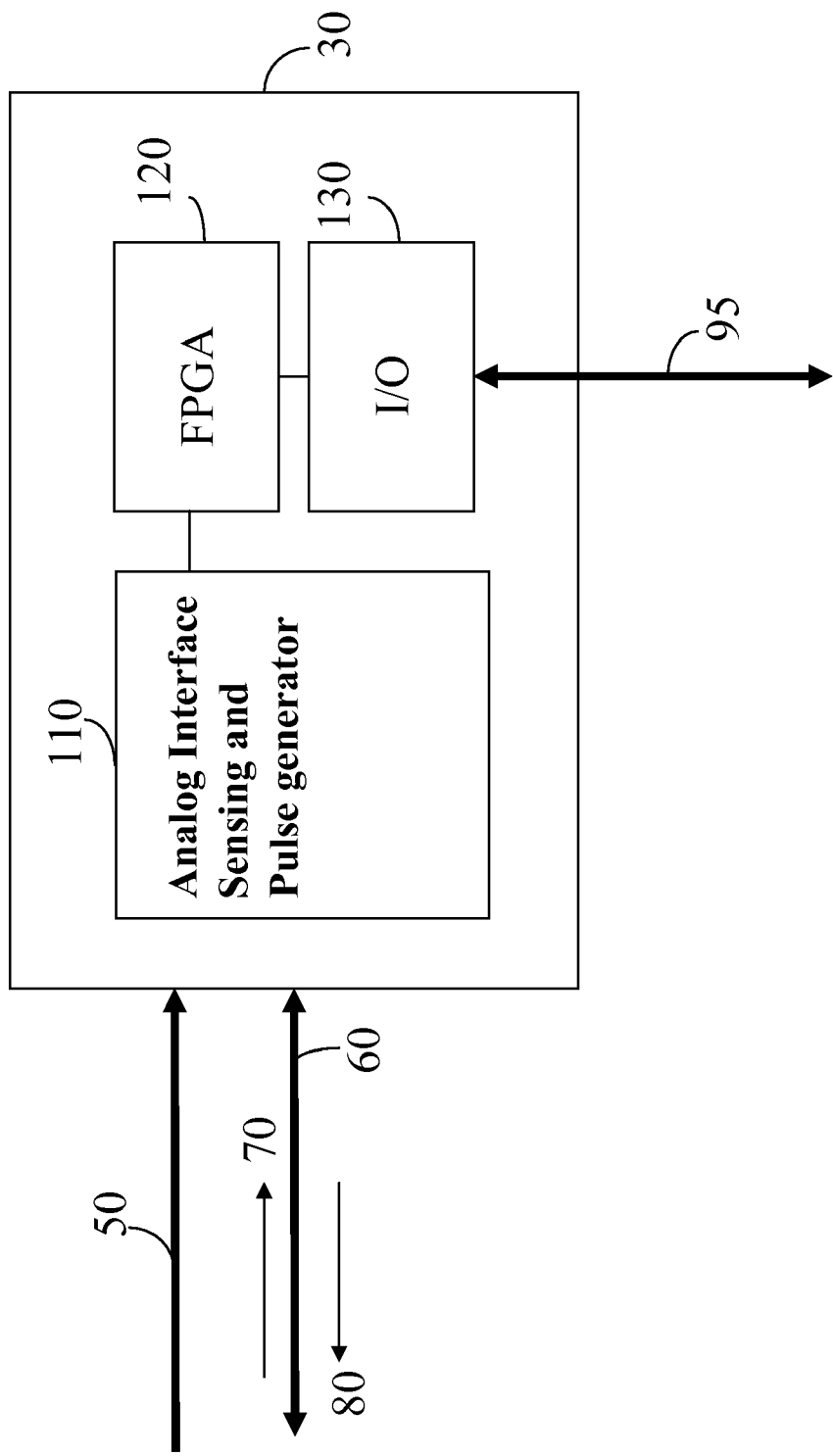
FIG. 2 illustrates a high level block diagram of an embodiment of the cardiac pacemaker prototyping board of FIG. 1.

FIG. 2 illustrates a high level block diagram of an embodiment of cardiac pacemaker prototyping board 30 of FIG. 1 comprising: an analog interface sensing and pulse generator 110; a field programmable gate array (FPGA) 120; an input/output device 130; a bidirectional data connection 95; a bidirectional IEGM path 60 carrying both a simulated IEGM 70 and a pacing stimulation 80; and a simulated hemodynamic sensor signal 50. FPGA 120 comprises the digital design of the pacemaker device control system and is connected to both input/output device 130 and analog interface sensing and pulse generator 110. FPGA 120 can implement for example both an adaptive CRT device learning module, a spiking neural network, and a deterministic controller of the pacemaker device as described in international patent application S/N PCT/IL2004/000659 published Jan. 25, 2005 as WO 2005/007075 entitled "Adaptive Resynchronization Therapy System" to Rom referenced above. Analog interface sensing and pulse generator 110 comprises an analog to digital interface that senses the electrical signals representative of the simulated electrical heart condition received via simulated IEGM 70 and the simulated mechanical heart condition via simulated hemodynamic sensor signal 50, amplifies and digitizes the incoming signals. Analog interface sensing and pulse generator 110 further comprises a pulse generator that stimulates heart simulator 20 through pacing stimulation 80.

Bidirectional data connection 95 may comprise a cable connection that allows for programming FPGA 120 from an external device via input/output device 130 to which it is connected. Bidirectional data connection 95 may further comprise a wireless data connection for uploading data accumulated in cardiac pacemaker prototyping board 30 and to receive programming instructions.

Figure 3:
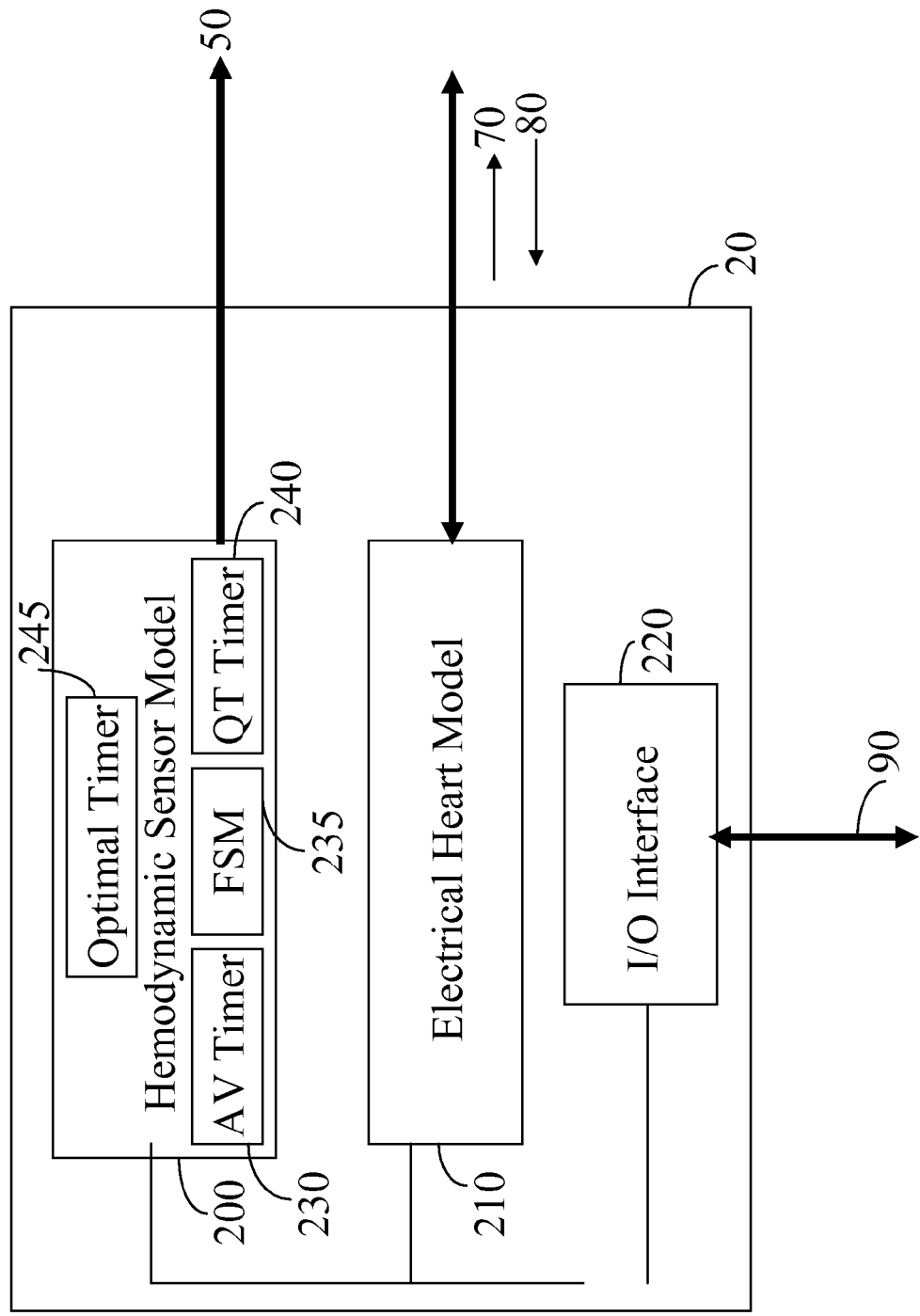
FIG. 3 illustrates a high level block diagram of a heart simulator in accordance with a principle of the current invention.

FIG. 3 illustrates a high level block diagram of a heart simulator 20 in accordance with a principle of the current invention comprising a hemodynamic sensor model 200, an electrical heart model 210, and input/output interface 220, a simulated hemodynamic sensor signal 50, a simulated IEGM 70, a pacing stimulation 80 and a bidirectional data path 90. Hemodynamic sensor model 200 comprises an AV timer 230, a finite state machine (FSM) 235, a QT timer 240 and an optimal timer 245. Electrical heart model 210 is operational to generate simulated IEGM 80 representative of a particular heart condition, and in particular the electrical behavior thereof. Hemodynamic sensor model 200 is operational to generate simulated hemodynamic sensor signal 50 representative of a particular heart condition, and in particular the mechanical behavior thereof as sensed by a particular specific implanted sensor. Bidirectional data from bidirectional data path 90 is connected to input/output interface 220 and input/output interface 220 is connected to each of hemodynamic sensor model 200 and electrical heart model 210. Electrical heart model 210 is in communication with hemodynamic sensor model 200.

Advantageously, various types and designs of hemodynamic sensor are modeled by hemodynamic sensor model 200 allowing for testing of cardiac pacemaker prototyping board 30 of FIG. 1 in combination with different types of sensors and sensor features. In one embodiment hemodynamic sensor model 200 comprises a model of one or more impedance sensors, in another embodiment hemodynamic sensor model 200 comprises a model of one or more pressure sensors, in another embodiment hemodynamic sensor model 200 comprises a model of one or more cardiac wall accelerometers, in another embodiment hemodynamic sensor model 200 comprises a model of one or more QT interval sensors, and in another embodiment hemodynamic sensor model 200 comprises a model of one or more non-invasive hemodynamic sensors. In another embodiment hemodynamic sensor model comprises a plurality of sensor types selected from impedance sensors, pressure sensors and accelerometers. Thus, different types of sensors and sensor features, in combination with different cardiac pacemaker architectures, optimization parameters and learning methods can be tested and verified using heart simulator 20, and only after satisfactory results are obtained, an application specific integrated circuit (ASIC) can be fabricated and tested in an implant device in animal and clinical trials which are both an orders of magnitude more time consuming and expensive.

There are several implanted hemodynamic sensors that are being developed by manufactures of pacemakers and others which are primarily targeted at closed loop implanted cardiac pacemaker devices. These hemodynamic sensors include, but are not limited to, ventricle impedance sensors, ventricle pressure sensors, cardiac wall acceleration sensors and QT interval sensors.

The present invention does not require modeling in detail the complete mechanical behavior of the heart in order to generate hemodynamic sensor model 200. Thus, there is no requirement for an electromechanical heart model that models each heart chamber behavior, each heart valve and cell conductance. Instead, hemodynamic sensor model 200 of the subject invention focuses only on modeling the specific sensor signal temporal patterns as a function of the heart condition and pacing interval. It is this information which will be sensed by the implanted device through the specific implanted sensors, and cardiac pacemaker prototyping board 30 is responsive to this input data. In a preferred embodiment hemodynamic sensor model 200 comprises a plurality of models, including a model for each type of sensor that will be used by cardiac pacemaker prototyping board 30.

The invention will hereinafter be described in detail in relation to an impedance sensor model, and in particular to a ventricle impedance sensor model, however this is by way of illustration only and is not meant to be limiting in any way. The invention is equally applicable to pressure sensors, accelerometers and interval sensory.

Hemodynamic sensor model 200 generates a temporal impedance signal. Stroke volume and pre-load volume measures can be extracted from the temporal impedance signal beat after beat. Hemodynamic sensor model 200 of the present invention preferably uses a state machine description of the sensor output with a pre-defined functional dependence of the main signal characteristics as will be explained below, however this is not meant to be limiting in any way. The use of fuzzy logic or parallel processing is specifically contemplated. AV timer 230, QT timer 240, FSM 235 and optimal timer 245 are each operational, as will be described further hereinto below, to generate sub-optimal states representative of sub-optimal pacing.

Figure 4:
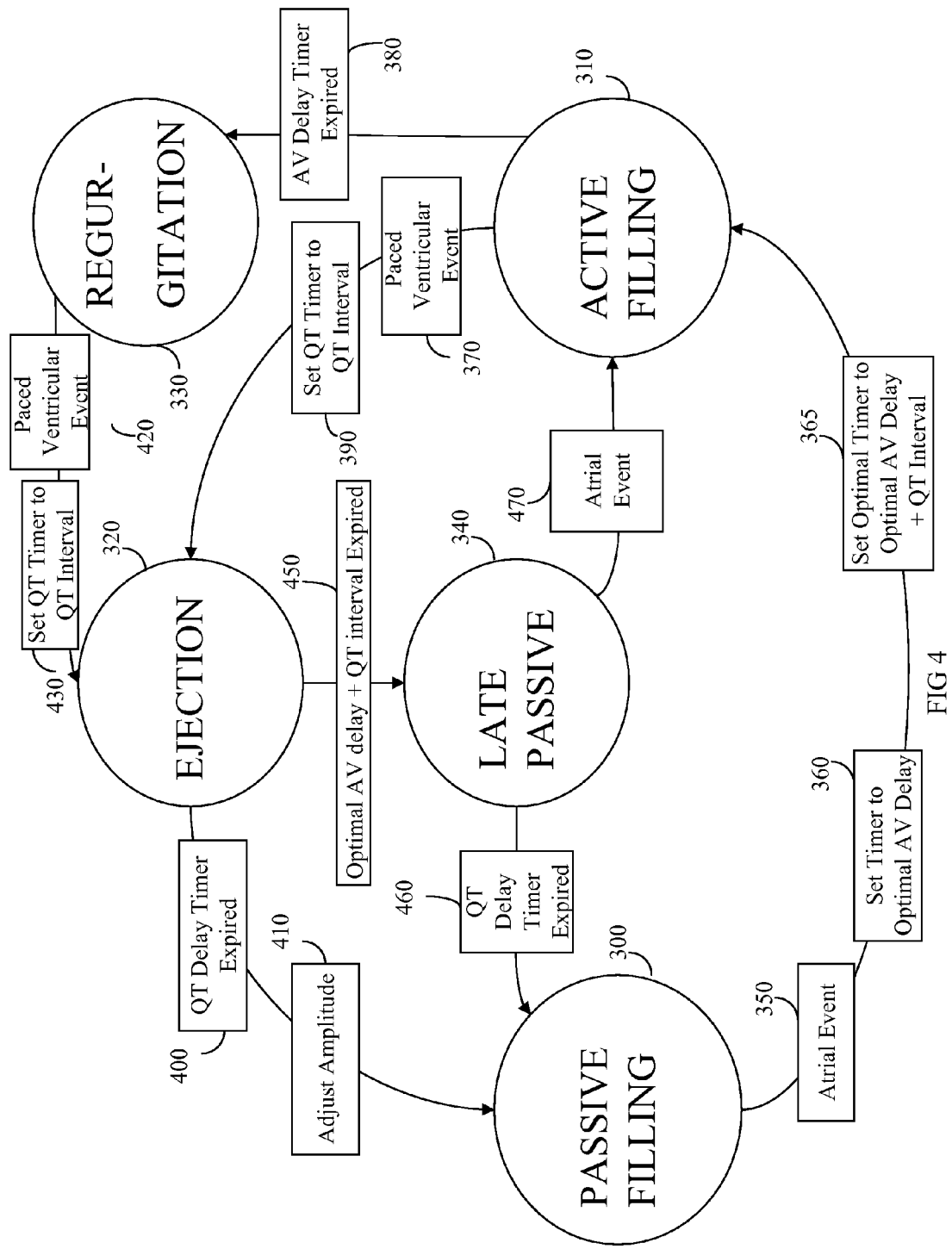
FIG. 4 illustrates a high level state machine representation of the hemodynamic sensor model of the heart simulator of FIG. 3 in accordance with a principle of the current invention.

FIG. 4 illustrates a high level state machine representation of hemodynamic sensor model 200 of heart simulator 20 in accordance with a principle of the current invention, and in an exemplary embodiment is implemented by FSM 235 of FIG. 3. FSM 235 exhibits 5 states, state 300 which simulates passive filling, state 310 which simulates active filling, state 320 which simulates ejection, state 330 which simulates regurgitation and state 340 which simulates late passive filing. The output of hemodynamic sensor 200 of FIG. 3 is a function of: the state in accordance with pre-defined formulas that describe the dependence of the impedance signals on various pre-defined functions; user set parameters such as heart rate, ventricle volume pre-load, optimal AV delay and QT delay that depend on heart rate; and the timing information of electrical heart model 210 such as a sensed atrial event and a sensed or paced ventricle event. Advantageously, electrical heart model 210 and hemodynamic sensor model 200 are responsive to pacing stimulation 80.

FSM 235 of hemodynamic sensor model 200 begins at passive filling state 300 and the impedance value output by hemodynamic sensor model 200 decreases with time in this state. It is to be understood that the impedance value decreases with time in passive filling state 300 since the ventricle is filling with blood and the heart impedance has an inverse relation to ventricle volume. When an atrial event 350 occurs, FSM 235 sets AV timer 230 of FIG. 3, as illustrated at state 360, with the optimal AV delay, as will be explained further hereinto below. In state 365 an optimal timer is loaded with the optimal AV delay plus the QT interval, as will be explained further hereinto below and makes a transition to active filling state 310.

Active filling state 310 is characterized by a decreasing impedance at an increased slope due to the fact that blood is drawn into the ventricle of the heart at an increased rate due to contraction of the atrium.

Active filling state 310 continues until either a paced ventricular event occurs, denoted as event 370, as determined by pacing stimulation 80, or AV timer 230 set by event 360 expires as denoted by event 380. In the event ventricular pacing event 370 occurs, FSM 235 sets QT timer 240 of FIG. 3, as illustrated at state 390, with a pre-determined QT interval, as will be explained further hereinbelow, and transitions to ejection state 320, as optimal behavior. In ejection state 320 the impedance value output by hemodynamic sensor model 200 begins to increase since in ejection state 320 the blood is ejected from the ventricle and the volume decreases resulting in increased impedance. In the event QT timer 240 of FIG. 3, loaded in state 390 with the pre-determined QT interval, expires, FSM 235 of hemodynamic sensor model 200 resets the amplitude in accordance with Eq. 2 described below as denoted by event 410 and transitions to passive filling state 300 as described above, thereby restarting the cycle, as optimal behavior.

In the event that in active filling state 310, AV timer 230 set in event 360 expires, i.e. the optimal AV delay has expired and a paced ventricular event has not occurred, FSM 235 of hemodynamic sensor model 200 transitions to regurgitation state 330 which is representative of backflow to the atrium as illustrated by event 380, as suboptimal behavior. In regurgitation state 330 the impedance increases since blood is backflowing to the atria resulting in a lower ventricular volume. Regurgitation state 330 is maintained until a paced ventricular event occurs, as denoted by event 420, and in response FSM 235 of hemodynamic sensor model 200 sets QT timer 240 of FIG. 3, as illustrated at event 430, with a pre-determined QT interval and transitions to ejection state 320.

In the event that in ejection state 320 optimal timer 245 set in state 365 expires, denoted event 450 and characteristic of ejection state 320 being entered late due to having experienced regurgitation state 330, FSM 235 of hemodynamic sensor model 200 transitions to late passive state 340. In late passive state 340 the impedance value output by hemodynamic sensor model 200 increases over time representative of late passive ejection of blood, however due to the delayed paced event, i.e since the AV timer 230 expired as described above in relation to state 380, ejection began too late and thus the impedance waveform will not reach the expected maximal amplitude in this cardiac cycle. This is representative of suboptimal ejection.

In the event that in late passive state 340 a right atrial event occurs, denoted event 470, FSM 235 transitions to active filling state 310 and sets both AV timer 230 and optimal timer 245 as described in relation to states 360, 365. In the event that in late passive state 340 QT timer 240 set in state 430 expires, denoted event 460, FSM 235 transitions to passive filling state 300.

Both regurgitation state 330 and late passive state 340 exhibit a reduced stroke volume as compared with optimal behavior, which exhibits an optimal stroke volume. As indicated above, stroke volume can be extracted from the temporal impedance signal. The stroke volume is represented by the difference between the maximum and minimum impedance amplitude as will be described further hereinto below.

As described above in relation to FIGS. 3 and 4 there are a few pre-defined characteristic functions and timers that determine the simulated temporal impedance signal waveform.

AV Timer

AV timer 230 of FIG. 3 is used to transition from active filling state 310 to regurgitation state 330 when the pre-defined optimal AV delay expired before a ventricular pacing event occurs. The pre-defined optimal AV delay depends on the cardiac cycle length set by the user, preferably utilizing computing device 40, through a simplified formula:

$$AV_{opt} = 160 * Cardiac\ Cycle/1000\ (msec) \quad \text{Eq. 1}$$

with the 160 representing a typical value for a normal AV interval at rest. The optimal AV delay, $AV_{opt}$, and any deviation from pacing in accordance with $AV_{opt}$ influences the simulated impedance waveform amplitude. The larger the deviation from $AV_{opt}$ the larger the deviation from the optimal impedance values as will be described further hereinto below.

QT Timer

QT timer 240 is used to transition from ejection state 320 to passive filling state 300 when QT timer 240 expires, at the pre-defined QT interval as shown by event 400, or to transition from late passive state 340 to passive filing state 300, as shown by event 460, if the pacing ventricular event 420 occurred late after the AV timer expired in regurgitation state 330. The pre-defined QT interval setting for QT timer 240 is a function of the user set cardiac cycle and is defined as the time between the beginning of the QRS complex to the end of the T-wave. In Table I below, in which the cardiac cycle is defined as the time between adjacent P waves or QRS complexes. The cardiac cycle is inversely proportional to the heart rate.

TABLE I

| QT Interval | Cardiac Cycle [msec] |
|---|---|
| 320 | 1023-992 |
| 315 | 991-960 |
| 310 | 959-928 |
| 305 | 927-897 |
| 300 | 896-865 |
| 295 | 864-833 |
| 290 | 832-801 |
| 285 | 800-769 |
| 280 | 768-737 |
| 275 | 736-705 |
| 270 | 704-673 |
| 265 | 672-641 |
| 260 | 640-609 |
| 255 | 608-577 |
| 250 | 576-545 |
| 245 | 544-513 |
| 240 | 512-481 |
| 235 | 480-449 |
| 230 | 448-417 |
| 225 | 416-385 |
| 220 | 384-353 |
| 215 | 352-321 |

Total Impedance Amplitude

The total impedance amplitude determines the simulated stroke volume and is a function of three parameters that change asynchronously during the operation of heart simulator 20: a) the pacing interval received from cardiac pacemaker prototyping board 30; b) the cardiac cycle time set by the user; and c) the Frank-Sterling factor. The total impedance amplitude is a sum of three contributions:

$$\text{Amplitude}_{Total} = \text{AMP}_{Pacing\_Intervals} + \text{AMP}_{Cardiac\_Cycle} + \text{AMP}_{Frank\_Starling} \quad \text{Eq. 2}$$

$\text{AMP}_{Pacing\_Intervals}$ depends on the pacing time interval of each heart beat as defined by $\text{AV}_{opt}$ of Eq. 1 above and measured relative to the sensed atrial event. Thus:

$$\text{Paced}_{AVdelay} = \text{AV}_{opt} - (\text{Atrial Event}(350) - \text{Ventricular Event}(370,420)) \quad \text{Eq. 3}$$

$$\text{AVDelay}_{effective} = \text{Paced}_{AVdelay} * 1000/\text{Cardiac Cycle} \quad \text{Eq. 4}$$

$$\text{AMP}_{pacing\_Intervals} = 100 - \tfrac{1}{2} * |160 - \text{AVDelay}_{effective}| \quad \text{Eq. 5}$$

where the value 100 of Eq. 5 represents the full scale of the $\text{AMP}_{Pacing\_Intervals}$ amplitude.

$\text{AMP}_{Cardiac\_Cycle}$ is a function of the cardiac cycle and is set forth in Table II below. The variable $\text{AMP}_{Cardiac\_Cycle}$ represents the contribution of the heart rate to the simulated to the simulated stroke volume. The stroke volume typically increases with increasing heart rate.

TABLE II

| $\text{Amp}_{Cardiac\_Cycle}$ | Cardiac Cycle [msec] |
|---|---|
| 0 | 1023-992 |
| 2 | 991-960 |
| 5 | 959-928 |
| 10 | 927-897 |
| 15 | 896-865 |
| 20 | 864-833 |
| 30 | 832-801 |
| 40 | 800-769 |
| 50 | 768-737 |
| 60 | 736-705 |
| 70 | 704-673 |
| 80 | 672-641 |
| 90 | 640-609 |
| 100 | 608-577 |
| 110 | 576-545 |
| 120 | 544-513 |
| 130 | 512-481 |
| 140 | 480-449 |
| 150 | 448-417 |
| 160 | 416-385 |
| 170 | 384-353 |
| 180 | 352-321 |

$$\text{AMP}_{Frank\_Sterling} = 50*(1 - \text{EDZ0}/31), 31 > \text{Load} > 0 \quad \text{Eq. 6}$$

EDZ0 is defined as the value of the impedance sensor when the ventricle is maximally filled, i.e. the end diastolic impedance at the end diastolic volume. EDZ0 is an input parameter selected to shift up or down the full impedance waveform so as to simulate various physiological conditions. As described above the Frank Starling principal defines a relationship between the stroke volume and the end diastolic volume, and indicates that a higher stroke volume is associated with a larger end diastolic volume. Thus adjusting the EDZ0 factor further enables simulating heart activity as a function of heart contractility. The unit 31 is defined is defined arbitrarily as the maximum value, and the unit 50 is also defined as the arbitrary maximum value for the Frank Starling amplitude value.

The impedance waveform signal output by hemodynamic sensor model 200 is composed of 3 or 4 segments according to the states described above in relation to FIG. 4. In each segment the waveform is produced as a straight line for simplicity, however this is not meant to be limiting in any way. The use of curves or a plurality of subsegments within a state is specifically contemplated and is within the scope of the invention. The slope of the line, or lines, within the segment is preferably recalculated every cardiac cycle responsive to user defined parameters and pacing intervals.

The impedance slope during passive filling state 300 is uniformly negative and is equal to ⅔ of the total amplitude, $\text{Amplitude}_{Total}$, divided by the time interval defined by Cardiac Cycle$-\text{AV}_{opt}-$QT Interval, with the variable ⅔ selected based on an assumed value that ⅔ of the total diastolic volume is due to passive filling. The impedance slope during active filling state 310 is negative and equal to ⅓ of the total amplitude, $\text{Amplitude}_{Total}$, divided by $\text{AV}_{opt}$. The slope during ejection state 320 is positive and is equal to total amplitude, $\text{Amplitude}_{Total}$, divided by QT Interval. The slope during both regurgitation state 330 and late passive state 340 is positive, with the slope being determined as a consequence of the severity of the mitral regurgitation condition being simulated.

The user is preferably provided with an input screen via computing platform 40 to enter a number of variables. In particular, and without limitation, the user may define the cardiac cycle time, i.e. the atrial rate. The cardiac cycle time defines the time interval between atrial events. The user may also define EDZ0 as described above. The user also may define $AV_{opt}$ at a predetermined heart rate, for example $AV_{opt}$ at 60 beats per minute. Preferably, hemodynamic sensor model 200 is operative to calculate $AV_{opt}$ as required for the actual heart rate, or cardiac cycle time in the absence of an override input from the user.

The pacemaker inputs to the simulated sensor model are: a) a paced AV interval of the right ventricular measured from the right atrial event; and b) a paced AV interval of the left ventricular measured from the right atrial event. The AV delay is defined as the delay from an atrial event that triggers filling of the atrium to a ventricular event that triggers blood ejection from the ventricle. The VV interval is defined as the interval between the pacing signal for the left ventricle to the pacing signal for the right ventricle. Thus, when the left ventricle is paced before the right ventricle the VV interval is negative. The VV Interval is defined as:

$$VV_{interval} = Paced_{left}AV - Paced_{right}AV [msec]. \quad \text{Eq. 7}$$

In an exemplary embodiment the hemodynamic sensor model further allows the insertion of a random noise to the output. The random noise is added to the amplitude of Eq. 2 to define an amplitude total with noise, denoted Amplitude-$_{Totalwithnoise}$ as:

$$Amplitude_{Totalwithnoise} = Amplitude_{Total} + AMP_{Random\ Noise} \quad \text{Eq. 8}$$

The random noise input as $AMP_{Random\ Noise}$ mimics all sources of noise that can affect the output of the actual hemodynamic sensors in-vitro. This ability to add random noise advantageously further allows for the testing of cardiac pacemaker prototyping board 30, and a control system being tested thereon, in realistic conditions.

Figure 5:
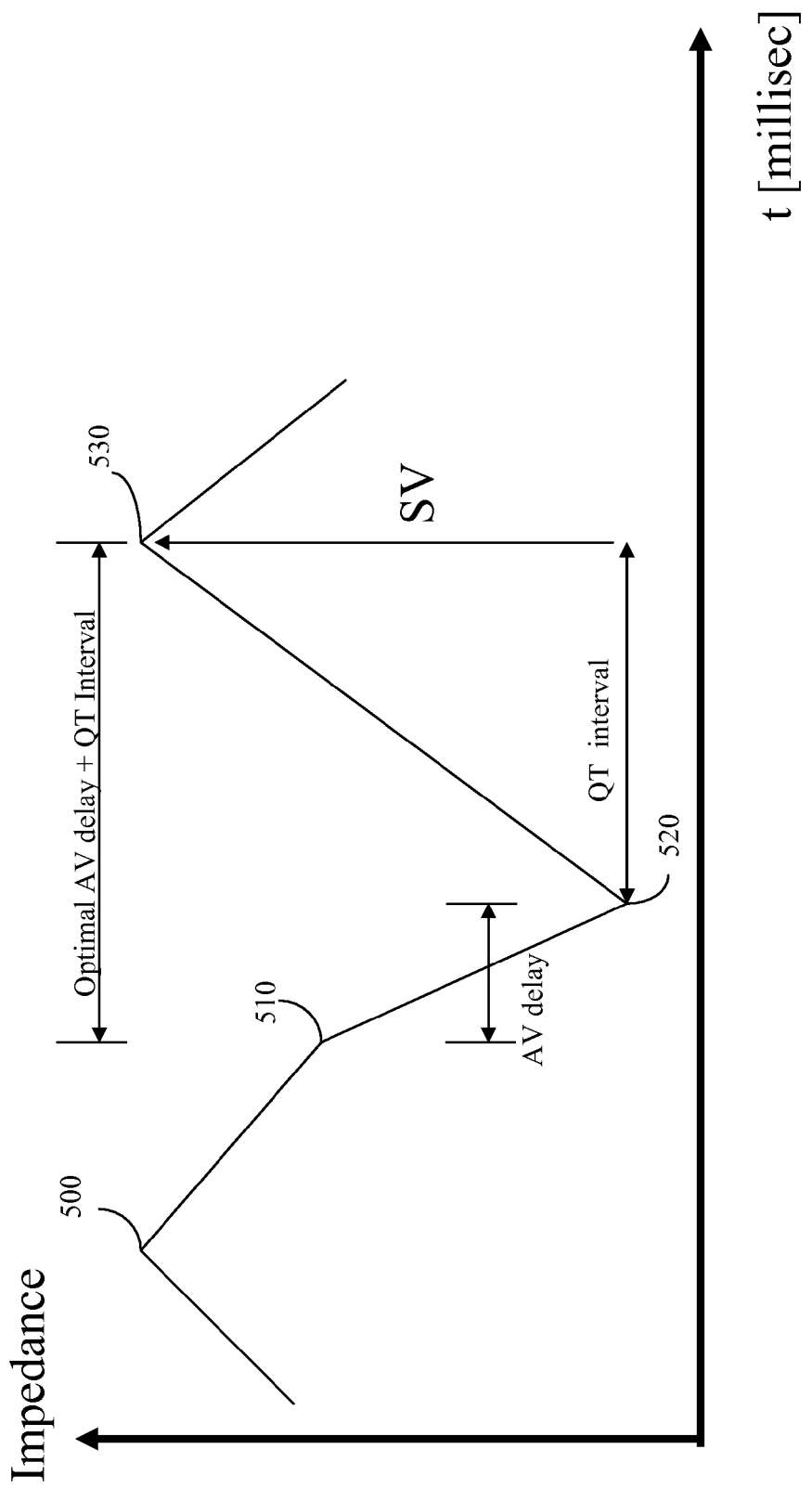
FIG. 5 illustrates an output of the hemodynamic sensor model simulating an impedance sensor in accordance with a principle of the current invention, the output being indicative of nominal heart operation.

FIG. 5 illustrates an output of the hemodynamic sensor model simulating an impedance sensor in accordance with the principle of the current invention, the output being indicative of nominal heart operation. The x-axis represents time in milliseconds and the y-axis represents a normalized impedance value. At point 500, expiration of a QT timer, which mimics a T-wave, triggers passive filling state 300 during which the impedance slope is negative from point 500 to point 510. Point 510 represents sensed atrial event 350 triggering the transition from passive filling state to active filling state 310. The slope from point 510 is more negative, characteristic of active filling state 310 which ends at point 520, representative of ventricular event 370. The delay between point 510 and point 520 is the $AV_{delay}$. The impedance at point 520 is at a minimum, indicative of maximum blood volume, and is defined as end diastolic volume (EDV).

The impedance slope from point 520 is positive, characteristic of ejection state 320 to point 530. Point 530 is representative of event 400, i.e. the expiration of the QT Interval. The impedance at point 530 is at a maximum indicative of a minimal blood volume, and is defined as end systolic volume (ESV). The stroke volume (SV) is proportional to the impedance differences:

$$\text{Stroke Volume} = f(Z_{ESV} - Z_{EDV}) \quad \text{Eq. 9}$$

Figure 6A:
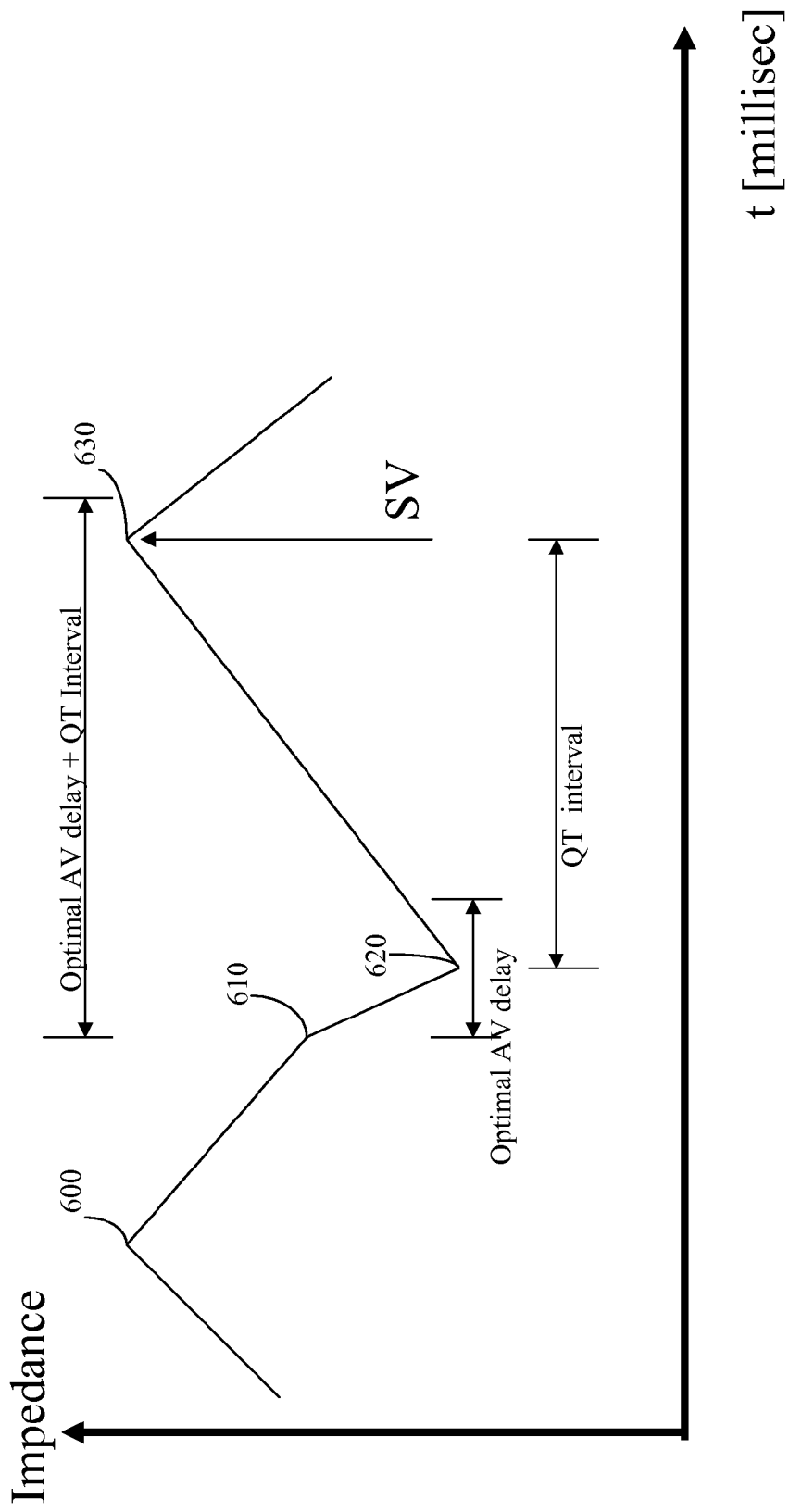
FIG. 6a illustrates an output of the hemodynamic sensor model simulating an impedance sensor in accordance with a principle of the current invention, the output being indicative of a short AV delay.

FIG. 6a illustrates an output of the hemodynamic sensor model simulating an impedance sensor in accordance with the principle of the current invention, the output being indicative of a too short AV delay. The short AV delay reduces the stroke volume due to sub-optimal too short filling phase. The x-axis represents time in milliseconds and the y-axis represents a normalized impedance value. At point 600, a QT timer triggers the passive filling state 300 during which the impedance slope is negative from point 600 to point 610. Point 610 represents atrial event 350 triggering the transition from passive filling state 300 to active filling state 310. The slope from point 610 is more negative, characteristic of active filling state 310 which ends at point 620, representative of ventricular event 370. It is to be noted that point 620 occurs earlier than desired, i.e. before the optimal $AV_{delay}$, $AV_{opt}$. The impedance at point 620 is at a minimum, indicative of maximum blood volume, i.e. EDV. Due to early triggering of point 620, EDV is not optimal.

The impedance slope from point 620 is positive, characteristic of ejection state 320 to point 630. Point 630 is representative of event 400, i.e. the expiration of the QT Interval. The impedance at point 630 is at a maximum indicative of a minimal blood volume, i.e. ESV. It is to be noted that due to the early triggering of point 620, SV of FIG. 6a is lower than the optimal timing SV of FIG. 5. The output signal as represented by FIG. 6a, and other temporal signals as required, may be further output to computing device 40 of FIG. 1 to enable the determination of various mechanical hemodynamic information such as, but not limited to, SV.

Figure 6B:
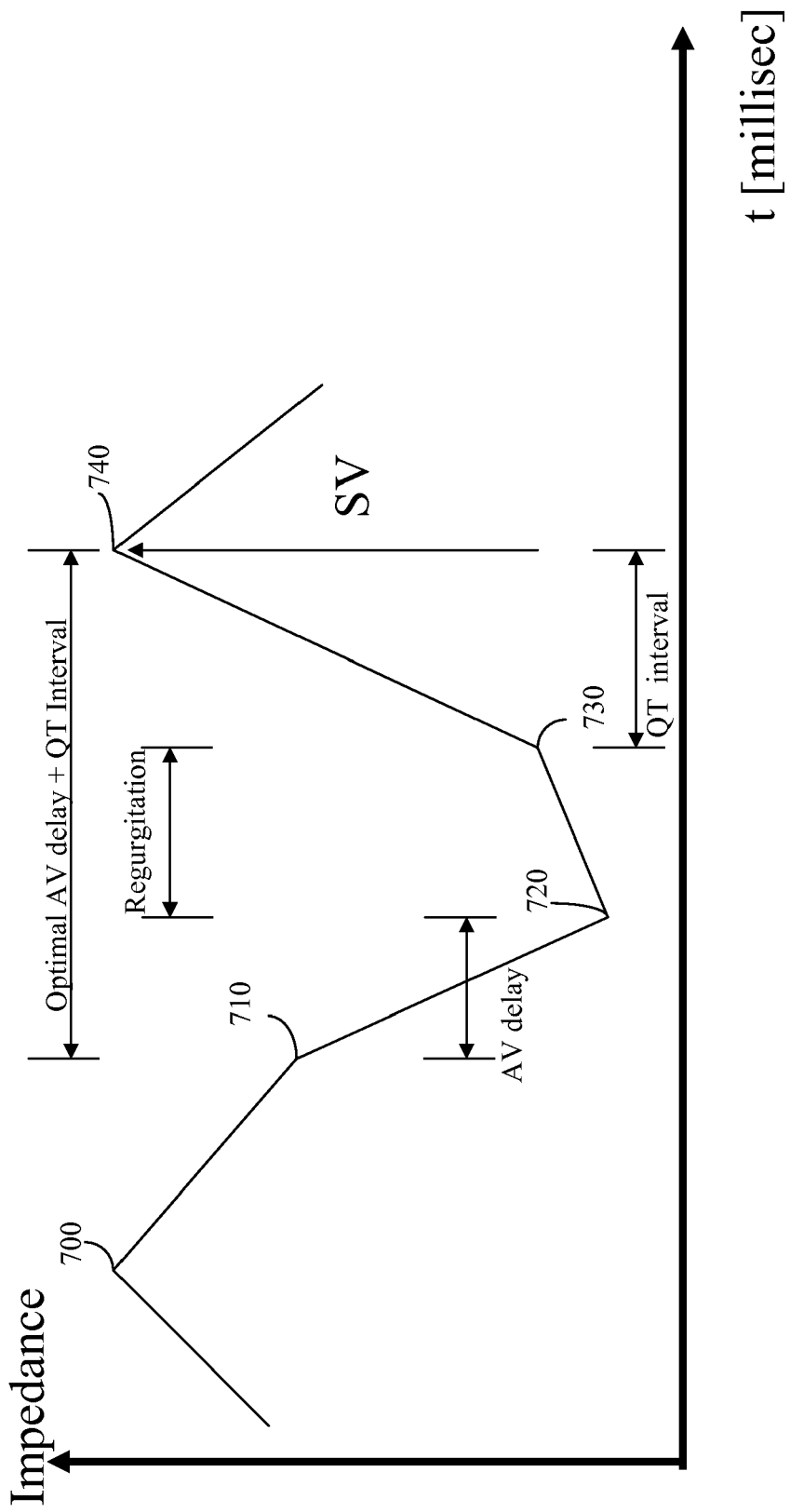
FIG. 6b illustrates an output of the hemodynamic sensor model simulating an impedance sensor in accordance with a principle of the current invention, the output being indicative of a long AV delay

FIG. 6b illustrates an output of the hemodynamic sensor model simulating an impedance sensor in accordance with the principle of the current invention, the output being indicative of a too long AV delay. The long AV delay reduces the SV due to regurgitation. The x-axis represents time in milliseconds and the y-axis represents a normalized impedance value. At point 700, a QT timer triggers passive filling state 300. The impedance slope is negative from point 700 to point 710 characteristic of passive filling state 300 which ends at point 710. Point 710 represents atrial event 350 triggering the transition from passive filling state 300 to active filling state 310. The slope from point 710 is more negative, characteristic of active filling state 310 which ends at point 720, representative of the expiration of AV timer 230, i.e. event 380 which triggers the transition to regurgitation state 330. The slope from point 720 is slightly positive characteristic of regurgitation state 330 and indicative of some blood escaping the ventrical due to regurgitation. The impedance at point 720 is at a minimum, indicative of maximum blood volume, i.e. EDV. The impedance increases from point 720 up to point 730 indicative of paced ventricular event 420, which transitions from regurgitation state 330 to ejection state 320.

Figure 7A:
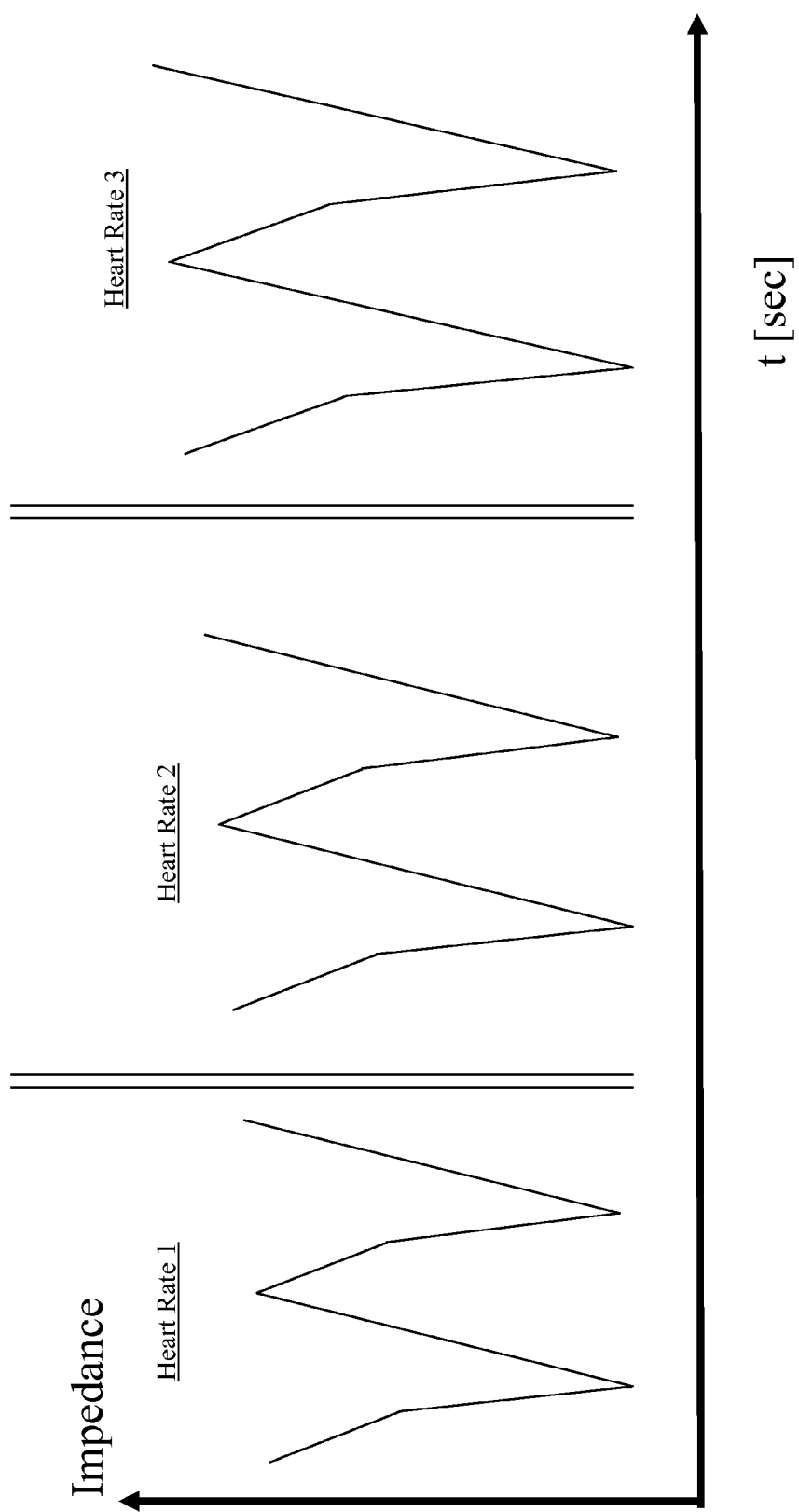
FIG. 7a illustrates the dependence of the output of the simulated impedance sensors of the hemodynamic sensor model on heart rate in accordance with a principle of the current invention.

The impedance slope from point 730 is strongly positive, characteristic of ejection state 320 to point 740. Point 740 is representative of event 400, i.e. the expiration of the QT Interval. The impedance at point 740 is at a maximum indicative of a minimal blood volume, i.e. ESV. It is to be noted that due to the late triggering of point 730, the SV is lower than the SV characteristic of the optimal timing of FIG. 5. The output signal as represented by FIG. 6b, and other temporal signals as required, may be further output to computing device 40 of FIG. 1 to enable the determination of various mechanical hemodynamic information such as, but not limited to, SV FIG. 7a illustrates the dependence of the output of the impedance sensors of the hemodynamic sensor model on HR in which the x-axis represents time in milliseconds and the y-axis represents impedance values. Three different impedance waves are shown denoted heart rate 1, heart rate 2 and heart rate 3. It is to be noted that heart rate 1<heart rate 2<heart rate 3. With increasing heart rate an increasing stroke volume and impedance range is exhibited.

Figure 7B:
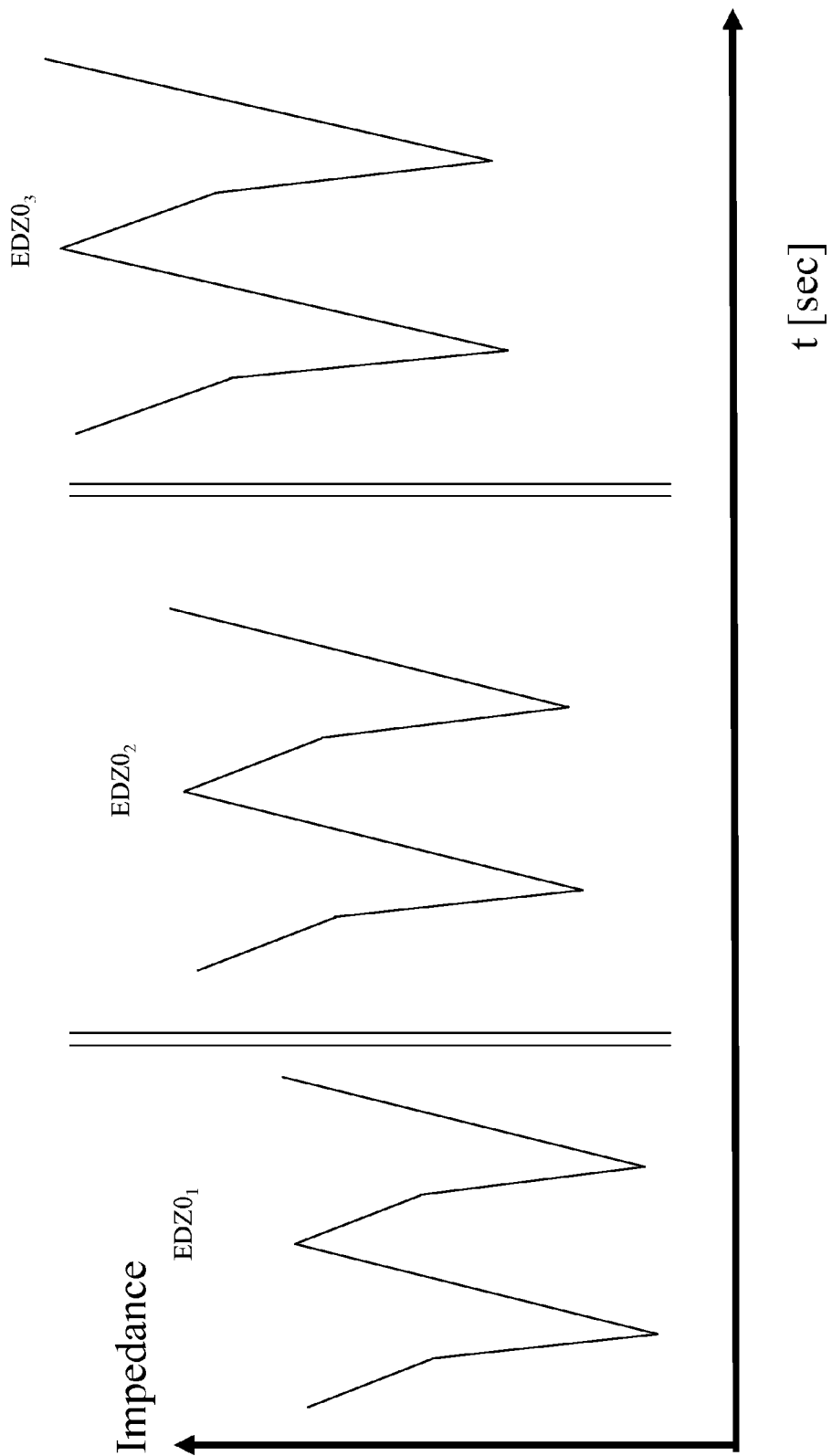
FIG. 7b illustrates the dependence of the output of the simulated impedance sensors of the hemodynamic sensor model on both heart rate and the end diastolic impedance parameter in accordance with a principle of the current invention.

FIG. 7b illustrates the dependence of the output of the impedance sensors of the hemodynamic sensor model on both HR and the end diastolic impedance parameter, EDZ0, in which the x-axis represents time in milliseconds and the y-axis represents impedance values. Three different EDZ0 values are illustrated denoted $EDZ0_1$, $EDZ0_2$ and $EDZ0_3$. If is to be noted that $EDZ0_1 > EDZ0_2 > EDZ0_3$. Thus as EDZ0 is reduced the entire impedance curve shifts upwards indicative of higher impedance values corresponding to lower ventricular volumes.

Thus the present embodiments enable a heart simulator that generates simulated implanted IEGM signals and hemodynamic sensor signals thereby simulating both heart electrical and mechanical activity, the simulation signals being responsive to the output of a CRT device. Preferably, the heart simulator further exhibits a programming input, allowing for simulation of various heart action irregularities.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

I claim:

1. A heart simulator exhibiting an output simulated hemodynamic sensor whose temporal pattern reflects a heart characteristic which is optimal when pacing stimulations are optimal, the heart simulator comprising:
    an input device arranged to provide at least one input parameter;
    a bidirectional intra-cardiac electrogram path;
    an electrical heart model in communication with said bidirectional intra-cardiac electrogram path, said electrical heart model arranged to output the simulated intra-cardiac electrogram via the bidirectional intra-cardiac electrogram path responsive to said provided at least one input parameter and the pacing stimulations received via said bidirectional intra-cardiac electrogram path; and
    a hemodynamic sensor model in communication with said electrical heart model and comprising an atrioventricular (AV) timer, an optimal timer and a QT timer, said hemodynamic sensor model arranged to output a simulated hemodynamic sensor signal, said hemodynamic sensor model arranged to load said AV timer with an optimal AV delay responsive to an atrial event of said electrical heart model, to load said optimal timer with the optimal AV delay plus a QT interval and to load said QT timer with the QT interval, each of the optimal AV delay and the QT interval responsive to the provided at least one input parameter, said hemodynamic sensor model exhibiting a plurality of distinct simulated heart states, and wherein said output simulated hemodynamic sensor signal exhibits a particular predetermined change over time in each of the distinct simulated heart states, and wherein transition between each of the distinct simulated heart states is responsive to one of said AV timer, said optimal timer and said QT timer in relation to events output by said electrical heart model.

2. A heart simulator according to claim 1, wherein said plurality of simulated heart states are selected from the group consisting of passive filling, active filling, ejection, regurgitation and late passive filling.

3. A heart simulator according to claim 1, wherein said at least one input parameter is selected from the group consisting of a heart rate value, a heart contractility value, a short AV delay and a long AV delay.

4. A heart simulator according to claim 1, wherein said hemodynamic sensor model simulates one of an impedance sensor, a pressure sensor, a cardiac wall accelerometer, a QT interval sensor and a non-invasive hemodynamic sensor.

5. A heart simulator according to claim 1, wherein said at least one input parameter comprises a cardiac cycle time.

6. A heart simulator according to claim 1, wherein said hemodynamic sensor model is further arranged to add a selectable amount of random noise to said output simulated hemodynamic sensor signal.

7. A heart simulator according to claim 1, wherein said plurality of distinct simulated heart states comprises an active filling state, an ejection state, a regurgitation state, a late passive state, and a passive filling state.

8. A heart simulator according to claim 7, wherein transition from said passive filling state is to said active filling state responsive to an atrial event output by said electrical heart model.

9. A heart simulator according to claim 7, wherein:
    transition from said active filling state is to said ejection state in the event that a ventricular event is output by said electrical heart model prior to expiration of said AV timer;
    transition from said active filling state is to said regurgitation state in the event that expiration of said AV timer occurs prior to a ventricular event being output by said electrical heart model; and
    transition from said regurgitation state is to said ejection state responsive to the ventricular event being output by said electrical heart model.

10. A heart simulator according to claim 7, wherein transition from said ejection state is to said passive filling state responsive to expiration of said QT timer while in said ejection state and is to said late passive state responsive to expiration of said optimal timer while in said ejection state, wherein transition from said late passive state is to said passive filling state responsive to expiration of said QT timer.

11. A heart simulator according to claim 7, wherein:
    transition from said passive filling state is to said active filling state responsive to an atrial event output by said electrical heart model;
    transition from said active filling state is to said ejection state in the event that a ventricular event is output by said electrical heart model prior to expiration of said AV timer;
    transition from said active filling state is to said regurgitation state in the event that expiration of said AV timer occurs prior to a ventricular event being output by said electrical heart model;
    transition from said regurgitation state is to said ejection state responsive to the ventricular event being output by said electrical heart model;

transition from said ejection state is to said passive filling state responsive to expiration of said QT timer while in said ejection state and is to said late passive state responsive to expiration of said optimal timer while in said ejection state; and transition from said late passive state is to said passive filling state responsive to expiration of said QT timer.

12. A development system for a cardiac pacemaker control system, said development system comprising:
- an input device arranged to provide at least one input parameter;
- a cardiac pacemaker prototype including an adaptive control system, said cardiac pacemaker prototype arranged to output pacing stimulations;
- a heart simulator in communication with said input device;
- a bidirectional intra-cardiac electrogram path connecting said cardiac pacemaker prototype to said heart simulator; and
- a simulated hemodynamic sensor signal connected between said heart simulator and said cardiac pacemaker prototype, said heart simulator comprising:
an electrical heart model in communication with said bidirectional intra-cardiac electrogram path, said electrical heart model arranged to output a simulated intra-cardiac electrogram via the bidirectional intra-cardiac electrogram path to said cardiac pacemaker prototype responsive to said provided at least one input parameter and pacing stimulations received via said bidirectional intra-cardiac electrogram path from said cardiac pacemaker prototype; and a hemodynamic sensor model in communication with said electrical heart model and comprising an atrioventricular (AV) timer, an optimal timer and a QT timer, said hemodynamic sensor model arranged to output the simulated hemodynamic sensor signal to said cardiac pacemaker prototype, said hemodynamic sensor model arranged to load said AV timer with an optimal AV delay responsive to an atrial event of said electrical heart model, to load said optimal timer with the optimal AV delay plus a QT interval and to load said QT timer with the QT interval, each of the optimal AV delay and the QT interval responsive to the provided at least one input parameter, said hemodynamic sensor model exhibiting a plurality of distinct simulated heart states, and wherein said output simulated hemodynamic sensor signal exhibits a particular predetermined change over time in each of the distinct simulated heart states, and wherein transition between each of the distinct simulated heart states is responsive to one of said AV timer, said optimal timer and said QT timer in relation to events output by said electrical heart model, wherein said output simulated hemodynamic sensor thereby exhibits a temporal pattern which reflects a heart characteristic which is optimal when the pacing stimulations are optimal.

13. A development system according to claim 12, wherein said plurality of heart states are selected from the group consisting of passive filling, active filling, ejection, regurgitation and late passive filling.

14. A development system according to claim 12, wherein said at least one input parameter is selected from the group consisting of a heart rate value, a heart contractility value, a short AV delay and a long AV delay.

15. The development system according to claim 12, wherein said hemodynamic sensor model simulates one of an impedance sensor, a pressure sensor, a cardiac wall accelerometer, a QT interval sensor and a non-invasive hemodynamic sensor.

16. The development system according to claim 12, wherein said plurality of distinct simulated heart states comprises an active filling state, an ejection state, a regurgitation state, a late passive state, and a passive filling state.

17. The development system according to claim 16, wherein transition from said passive filling state is to said active filling state responsive to an atrial event output by said electrical heart model.

18. The development system according to claim 16, wherein:
- transition from said active filling state is to said ejection state in the event that a ventricular event is output by said electrical heart model prior to expiration of said AV timer;
- transition from said active filling state is to said regurgitation state in the event that expiration of said AV timer occurs prior to a ventricular event being output by said electrical heart model; and
- transition from said regurgitation state is to said ejection state responsive to the ventricular event being output by said electrical heart model.

19. The development system according to claim 16, wherein transition from said ejection state is to said passive filling state responsive to expiration of said QT timer while in said ejection state and is to said late passive state responsive to expiration of said optimal timer while in said ejection state, wherein transition from said late passive state is to said passive filling state responsive to expiration of said QT timer.

20. The development system according to claim 16, wherein,
- transition for said passive filling state is to said active filling state responsive to an atrial event output by said electrical heart model;
- transition from said active filling state is to said ejection state in the event that a ventricular event is output by said electrical heart model prior to expiration of said AV timer;
- transition from said active filling state is to said regurgitation state in the event that expiration of said AV timer occurs prior to a ventricular event being output by said electrical heart model;
- transition from said regurgitation state is to said ejection state responsive to the ventricular event being output by said electrical heart model;
- transition from said ejection state is to said passive filling state responsive to expiration of said QT timer while in said ejection state and is to said late passive state responsive to expiration of said optimal timer while in said ejection state; and
- transition from said late passive state is to said passive filling state responsive to expiration of said QT timer.

* * * * *